US012760265B2

(12) United States Patent
Chen et al.

(10) Patent No.: US 12,760,265 B2

(45) Date of Patent: Oct. 13, 2026

(54) DYNAMIC HYDROGEL AND PULMONARY FIBROSIS BIONIC CHIP

(71) Applicant: Anivance AI Corporation, Hsinchu County (TW)

(72) Inventors: Guan-Yu Chen, Hsinchu County (TW); Jia-Wei Yang, Taoyuan City (TW); Chuan-Yi Yang, Keelung City (TW)

(73) Assignee: Anivance AI Corporation, Hsinchu County (TW)

( * ) Notice: Subject to any disclaimer, the term of this patent is extended or adjusted under 35 U.S.C. 154(b) by 0 days.

(21) Appl. No.: 18/677,911

(22) Filed: May 30, 2024

(65) Prior Publication Data

US 2025/0333682 A1 Oct. 30, 2025

(30) Foreign Application Priority Data

Apr. 26, 2024 (TW) ................................ 113115681

(51) Int. Cl.

| | |
|---|---|
| ***C12M 1/34*** | (2006.01) |
| ***C12M 1/12*** | (2006.01) |
| ***C12M 3/00*** | (2006.01) |
| ***C12M 3/06*** | (2006.01) |
| ***C12N 5/00*** | (2006.01) |
| *G01N 33/50* | (2006.01) |

(52) U.S. Cl.

CPC ............ *C12M 41/46* (2013.01); *C12M 21/08* (2013.01); *C12M 23/16* (2013.01); *C12M 25/02* (2013.01); *C12N 5/0068* (2013.01); *C12N 2539/10* (2013.01); *G01N 33/5082* (2013.01)

(58) Field of Classification Search

None

See application file for complete search history.

(56) References Cited

U.S. PATENT DOCUMENTS

2022/0218867 A1 7/2022 Sheikhi

FOREIGN PATENT DOCUMENTS

| | | | |
|---|---|---|---|
| CN | 117883629 | A | 4/2024 |
| JP | 2023-90746 | A | 6/2023 |
| TW | 201803603 | A | 2/2018 |

OTHER PUBLICATIONS

Zhang et al. Synthesis and characterization of multi-responsive poly(N-isopropylacrylamide)-sodium alginate-graphene oxide composite hydrogels. Polymer Bull. 80, 10825-10842 (2023) (Year: 2023).*

(Continued)

*Primary Examiner* — Sanza L. McClendon

(74) *Attorney, Agent, or Firm* — Winston Hsu

(57) ABSTRACT

This invention provides a dynamic hydrogel that may deform in response to heat, the dynamic hydrogel is composed of a hydrogel composition and is obtained by cross-link reaction. The hydrogel composition includes photo initiator, PNIPAM, GelMA and annealed graphene oxide. Based on the weight of the hydrogel composition being 100 wt %, the content of the annealed graphene oxide is between 0.03 wt % to 0.15 wt % and the XPS absorption intensity ratio of $sp^2$-C and $sp^3$-C ($sp^2$-C/$sp^3$-C) is greater than 1. Meanwhile, this invention also provides a pulmonary fibrosis bionic chip containing the dynamic hydrogel.

9 Claims, 11 Drawing Sheets

(7 of 11 Drawing Sheet(s) Filed in Color)

(56) References Cited

OTHER PUBLICATIONS

Huang et al. A Biomimetic Bilayer Hydrogel Actuator Based on Thermoresponsive Gelatin Methacryloyl-Poly(N-isopropylacrylamide) Hydrogel with Three-Dimensional Printiablity. ACS Applied Materials Interfaces 2023, 15, 4, 5798-5810 (Year: 2023).*
Peng et al. Thermoresponsive Deformable Actuators Prepared by Local Electrochemical Reduction of Poly(N-isopropylacrylamide)/Graphene Oxide Hydrogels. ACS Applied Nano Materials 2018, 1, 4, 1522-1530 (Year: 2018).*
Yang et al. Reduced Graphene Oxide-Containing Smart Hydrogels with Excellent Electro-Response and Mechanical Properties for Soft Actuators. ACS Appl. Materials Interfaces 2017, 9, 18, 15758-15767 (Year: 2017).*

* cited by examiner

DYNAMIC HYDROGEL AND PULMONARY FIBROSIS BIONIC CHIP

BACKGROUND OF THE INVENTION

1. Field of the Invention

The present invention relates to a dynamic hydrogel and a bionic chip, particularly to a thermosensitive dynamic hydrogel and a lung fibrosis bionic chip containing the dynamic hydrogel.

2. Description of the Prior Art

Idiopathic pulmonary fibrosis (IPF) is a chronic disease in which the progression of fibrosis in patients' lungs results in fibrotic characteristics resembling thread-like structures observable in the external appearance of the lungs or in lung computed tomography (CT) images. This progression leads to a severe decline in lung function. Currently, due to the limited efficacy of pharmacological treatments for IPF, in addition to various clinical studies, in vitro chip models have been established using different lung chip models to simulate the progression of lung fibrosis disease, as well as to evaluate the efficacy of drugs.

However, the human lung possesses a complex and intricate tissue structure. At rest, a healthy individual's lungs typically expand with a respiratory frequency of 10 to 12 breaths per minute. During normal respiration, the basement membrane undergoes an average linear strain expansion of approximately 4%, whereas during deep inhalation, distal tissues can experience linear strains of up to 12%. Additionally, the stiffness of healthy human lungs is approximately 2 kPa. In numerous pulmonary fibrosis diseases, pathological accumulation of extracellular matrix (ECM) proteins secreted by epithelial cells and fibroblasts leads to the stiffening of fibrotic tissues (typically with a stiffness of about 16 kPa). This stiffening results in increased resistance to airway inflation, thereby reducing mechanical strain in the parenchymal regions. Consequently, establishing an in vitro lung chip model that accurately simulates these conditions presents significant challenges.

In recent years, biomimetic technologies for constructing organs on chips have been developed. However, constructing an in vitro model that more closely simulates the human pulmonary fibrosis environment for the purpose of modeling the progression of pulmonary fibrosis diseases and evaluating the efficacy of drugs remains an extremely challenging task for professionals in the relevant technical fields.

SUMMARY OF THE INVENTION

Therefore, the objective of the present invention is to provide a dynamic hydrogel capable of thermally responsive deformation.

Thus, the dynamic hydrogel of the present invention is obtained by photo-crosslinking a hydrogel composition. The hydrogel composition includes a photoinitiator, poly (N-isopropyl acrylamide) (PNIPAM), gelatin methacryloyl (GelMA), and annealed graphene oxide (AGO).

Additionally, another objective of the present invention is to provide a lung fibrosis bionic chip having a dynamic hydrogel capable of thermally responsive deformation.

Therefore, the lung fibrosis bionic chip includes a chip body and the aforementioned dynamic hydrogel.

The chip body includes a substrate and at least one through-hole. The substrate has a first surface and a second surface opposing each other along a height direction. The diameter of the at least one through-hole ranges from 1 mm to 5 mm, extends along the height direction, is located within the substrate, and at least one end is open to the exterior.

The dynamic hydrogel is filled into the at least one through-hole and deforms upon heating.

The efficacy of the present invention lies in the addition of GelMA and AGO to the hydrogel composition. AGO possesses enhanced photothermal conversion capabilities, and when combined with GelMA, it further controls the hardness of the resulting dynamic hydrogel. This allows for the simulation of varying stiffnesses associated with different lung fibrosis conditions. Therefore, utilizing the dynamic hydrogel as an ECM-mimicking material in the lung fibrosis bionic chip enhances the deformation temperature of the hydrogel and simulates different stiffness ranges of pulmonary diseases, making the lung fibrosis bionic chip more suitable for use as an in vitro model that closely mimics the human lung fibrosis environment.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other features and advantages of the present invention will be clearly illustrated in the embodiments described with reference to the accompanying drawings, wherein:

FIG. 7 is a temperature measurement diagram illustrating the temperature measurements of crosslinked PNIPAM, P-AGO0.0375, and P-AGO0.075 after laser irradiation, wherein:

FIG. 7(*a*) shows the temperature measurements obtained using an infrared thermal imaging camera;

FIG. 7(*b*) shows the temperature variation curves at different laser irradiation durations;

FIG. 8 is a temperature measurement diagram illustrating the temperature variations of dynamic hydrogels irradiated by a laser at different UV irradiation times, wherein:

FIG. 8(*a*) shows the temperature measurements obtained using an infrared thermal imaging camera;

FIG. 8(*b*) shows the temperature variation curves at different laser irradiation durations;

DETAILED DESCRIPTION

Figure 1:
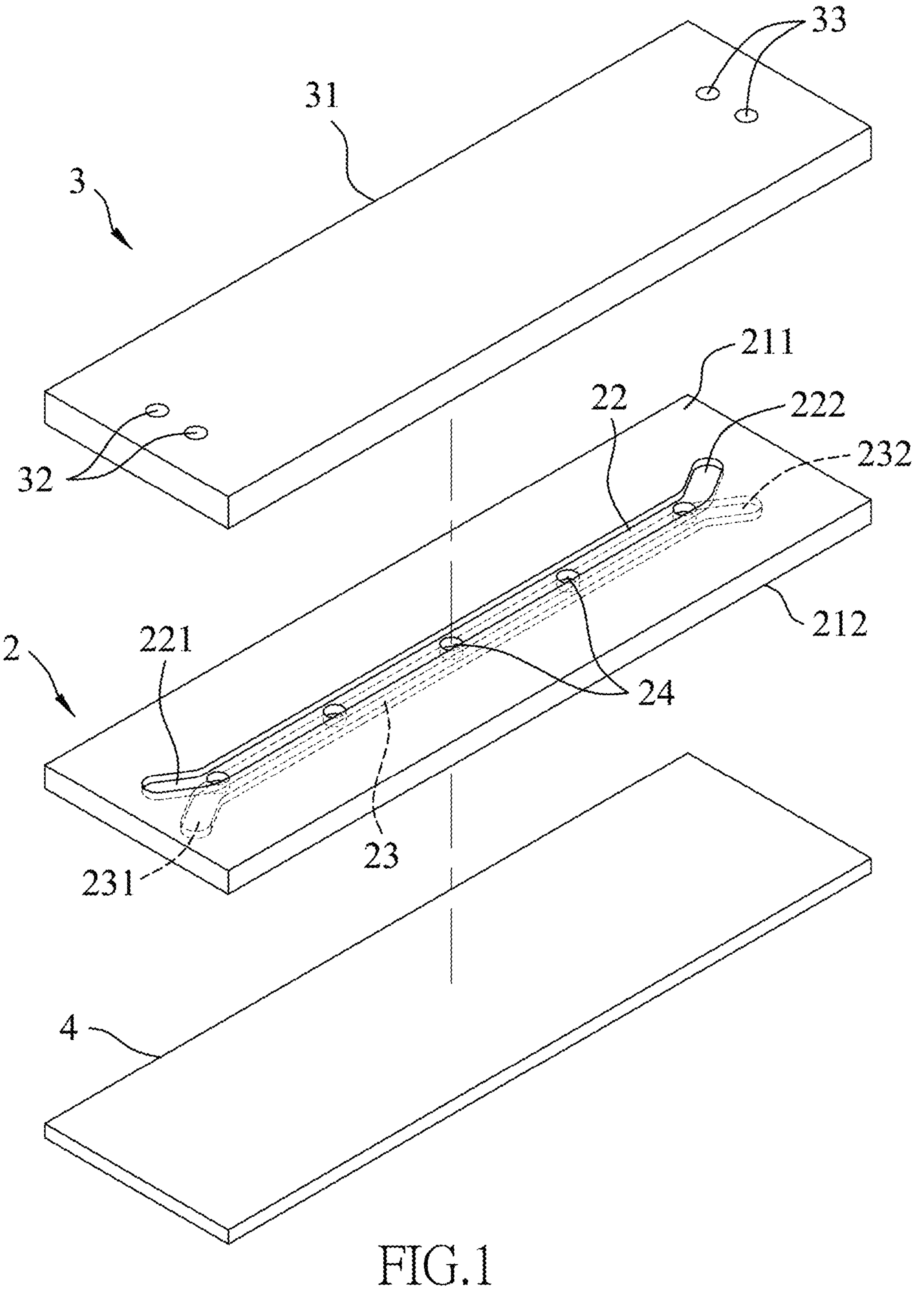
FIG. 1 is a partial cross-sectional schematic diagram illustrating an embodiment of the lung fibrosis bionic chip of the present invention.

Before the present invention is described in detail, it should be noted that similar components are indicated by the same reference numerals in the following descriptions.

The present invention provides a lung fibrosis bionic chip that incorporates a dynamic hydrogel with controllable and reversible deformation properties. The dynamic hydrogel enables the simulation of the ECM stiffness range found within the physiological environment of the lungs (7 kPa to 25 kPa). Furthermore, by utilizing a laser device to mimic dynamic responses corresponding to human respiratory frequencies (0.17 Hz to 0.3 Hz), the chip effectively recreates the dynamic microenvironment associated with alveolar expansion and contraction. Consequently, this facilitates the establishment of a cell-based ex vivo model that accurately replicates the in vivo conditions of lung fibrosis.

Figure 2:
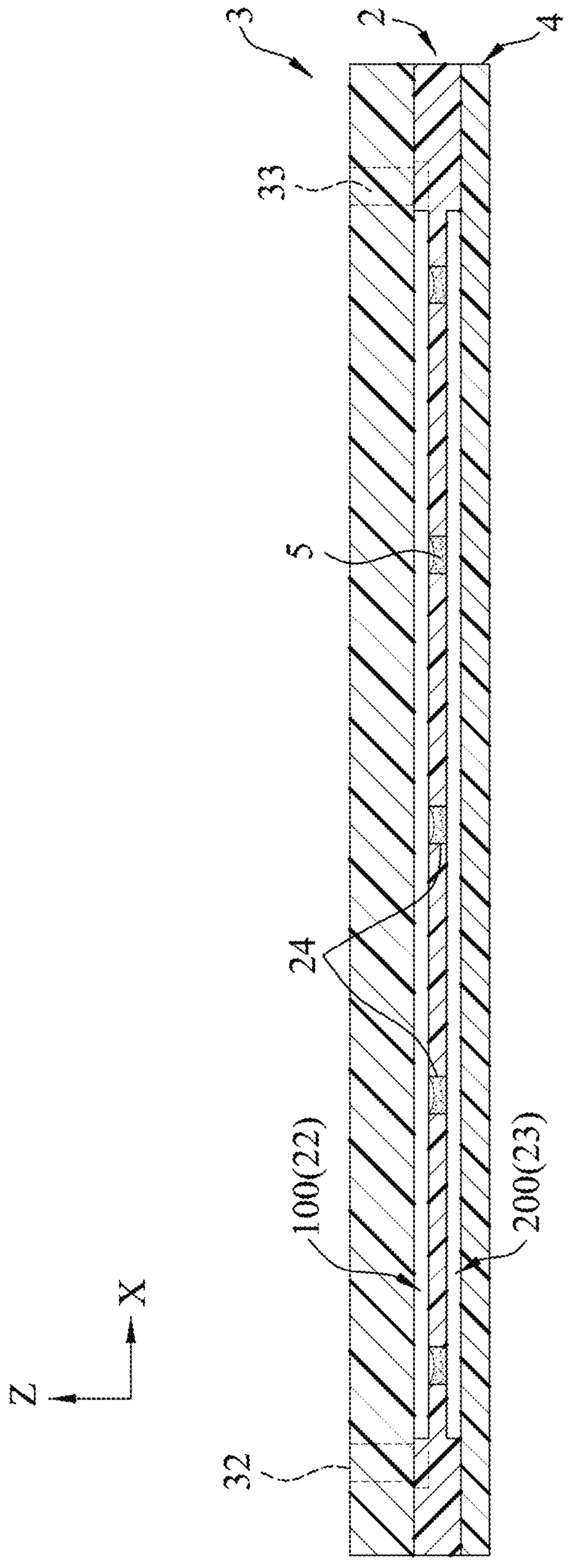
FIG. 2 is a flowchart illustrating the preparation process of the lung fibrosis bionic chip according to the embodiment of the present invention.

Referring to FIGS. 1 and 2, an embodiment of the lung fibrosis Hz chip includes a chip body 2, an upper cover 3, a backplate 4, and a dynamic hydrogel 5.

The chip body 2 includes a substrate 21, two grooves (a first groove 22 and a second groove 23), and at least one through-hole 24. Specifically, the substrate 21 has a first surface 211 and a second surface 212 opposing each other along a height direction Z. The first groove 22 and the second groove 23 are recessed from the first surface 211 and the second surface 212, respectively. The at least one through-hole 24 is located inside the substrate 21 and extends in the height direction Z. Both ends of the at least one through-hole 24 communicate with the first groove 22 and the second groove 23, with a diameter ranging from 1 mm to 5 mm.

It is to be noted that the diameter of the through-hole 24 is controlled to enable the dynamic hydrogel 5 placed therein to mimic the curvature of lung fibrotic structures, thereby closely resembling lung fibrotic structures and facilitating the establishment of cell-based ex vivo models. Preferably, the diameter of the through-hole 24 ranges from 1 mm to 3 mm.

In this embodiment, the chip body 2 including multiple through-holes 24 arranged linearly along the length direction X of the substrate 21, with each through-hole 24 having a diameter of 2 mm and a height of 0.6 mm is used as an example. The first groove 22 and the second groove 23 are parallel to each other at positions corresponding to the through-holes 24, thereby forming a Y-shaped structure at both ends where they intersect. The liquid inlet ends 221 and 231, and the liquid outlet ends 222 and 232, are respectively located at the opposite ends of the first groove 22 and the second groove 23, as examples. However, the actual implementation is not limited to this quantity and distribution pattern.

The upper cover 3 includes a cover body 31, multiple liquid inlet holes 32, and multiple liquid outlet holes 33 that penetrate the two opposite surfaces of the cover body 31. The cover body 31 connects to the first surface 211 of the substrate 21 and covers the first groove 22, thereby forming a first flow channel 100 in conjunction with the first groove 22. The liquid inlet holes 32 correspond to the liquid inlet ends 221 and 231 of the first groove 22 and the second groove 23, respectively, and communicate with the corresponding liquid inlet ends 221 and 231. The liquid outlet holes 33 correspond to the liquid outlet ends 222 and 232 of the first groove 22 and the second groove 23, respectively, and communicate with the corresponding liquid outlet ends 222 and 232.

The backplate 4 is connected to the second surface 212 of the substrate 21 and covers the second groove 23, thereby forming a second flow channel 200 in conjunction with the second groove 23.

The material of the substrate 21 may be polydimethylsiloxane (PDMS), and the upper cover 3 and the backplate 4 may be made of polyacrylate, such as polymethyl methacrylate (PMMA). The bonding surfaces between the substrate 21 and the upper cover 3 and backplate 4 are modified and then subjected to pressure to produce an irreversible reaction, thereby achieving stable and long-lasting bonds suitable for a dynamic system capable of long-term cell culture. The first flow channel 100 and the second flow channel 200, formed by the combination of the chip body 2 with the upper cover 3 and the backplate 4, drive the culture medium to flow during the modeling process to simulate blood flow, thereby mimicking the closed loop of the human circulatory system for cell culture within the chip body 2. This integration results in a more bionic alveolar microenvironment system.

The dynamic hydrogel 5 is placed in the through-holes 24 and deforms along the height direction Z when heated.

Specifically, the dynamic hydrogel 5 is formed by filling the hydrogel composition into the through-holes 24 and then crosslinking by exposure to light. The dynamic hydrogel 5 obtained after photo-crosslinking possesses a porous microstructure, with the degree of crosslinking and pore size of the porous microstructure controlled by the exposure time. This allows for the simulation of different lung stiffnesses.

Specifically, thermosensitive hydrogels respond to changes in external temperature. PNIPAM hydrogel, a typical thermosensitive hydrogel, has a lower critical solution temperature (LCST) around human physiological temperature (32° C. to 40° C.), where it undergoes a volume phase transition depending on its structure and molecular weight. GelMA enhances biocompatibility, mimics ECM deposition, and increases the LCST temperature, thereby raising the deformation temperature of the dynamic hydrogel 5 and simulating the stiffness range of lung diseases. AGO aids in forming the hydrogel network, facilitating material exchange and swelling absorption within the dynamic hydrogel 5. Since annealing does not affect the structure of graphene oxide (GO) (does not lose an oxygen functional group) but enhances its light absorption capacity, AGO is more efficient at driving PNIPAM deformation when exposed to light enabling the electrons of $sp^2$ to be oscillated. Thus, the hydrogel composition primarily utilizes PNIPAM, supplemented with GelMA for biocompatibility and stiffness control, and AGO for improved photothermal conversion efficiency, thereby enhancing the thermal response effect of the dynamic hydrogel 5.

Specifically, the hydrogel composition includes a photoinitiator, PNIPAM, GelMA, and AGO. The AGO is obtained by annealing graphene oxide (GO) at 80° C. for 1 to 5 days. The XPS absorption spectrum of the AGO exhibits a $sp^2$-C/$sp^3$-C absorption intensity ratio ($sp^2$-C/$sp^3$-C) greater than 1.

In this embodiment, the AGO is obtained by annealing graphene oxide (GO) at 80° C. for 5 days.

In some embodiments, the dynamic hydrogel 5 exhibits a volume deformation of no less than 20% when heated from room temperature to a temperature above the LCST of PNIPAM after reaching swelling equilibrium. Additionally, the XPS absorption spectrum of the AGO shows a $sp^2$-C/$sp^3$-C absorption intensity ratio ($sp^2$-C/$sp^3$-C) ranging between 1.09 and 1.3.

Furthermore, by controlling the UV irradiation time of the hydrogel composition, the pore size of the resulting porous structure may be adjusted, thereby modifying the hardness of the dynamic hydrogel 5 to simulate the physiological hardness of lung fibrosis ECM. For example, UV irradiation at 365 nm and 100 mW for 10 to 25 minutes may simulate the physiological hardness of lung fibrosis ECM (7 kPa to 25 kPa).

In some embodiments, based on a weight percentage of 100 wt % for the hydrogel composition, the content of gelatin methacryloyl (GelMA) ranges from 3 wt % to 8 wt %, and the content of AGO ranges from 0.03 wt % to 0.1 wt %.

In some embodiments, based on a weight percentage of 100 wt % for the hydrogel composition, the content of gelatin methacryloyl (GelMA) ranges from 3 wt % to 5 wt %, and the content of AGO ranges from 0.0375 wt % to 0.1 wt %. In this embodiment, the content of gelatin methacryloyl is 5 wt % as an example.

With reference to FIG. 2, the preparation method for the aforementioned embodiment of the lung fibrosis bionic chip is described as follows:

Hydrogel Composition Preparation: Add the AGO stock solution (4 mg/ml) to dimethyl sulfoxide (DMSO) and dilute to obtain an AGO mixture at 3 mg/ml. Next, transfer the AGO mixture to a centrifuge tube and mix uniformly using a vortex mixer. Subsequently, add 0.5 wt % N,N-methylenebisacrylamide (BIS) and 0.5 wt % photoinitiator (2-Hydroxy-4'-(2-hydroxyethoxy)-2-methylpropiophenone). Following this, sequentially add 10 wt % PNIPAM and 5 wt % gelatin methacryloyl (GelMA), and mix uniformly with a vortex mixer for approximately 30 minutes to obtain the hydrogel composition.

Chip Body 2 Preparation: Mix silicone oligomer (DOW CORNING SYLGARD 184) and PDMS in a 10:1 ratio to obtain a PDMS mixture. Degas the PDMS mixture under vacuum. Subsequently, pour the degassed PDMS mixture into a mold designed to form the chip body structure. Cure the mixture at 60° C. for 4 hours, then demold to obtain the chip body.

Upper Cover 3 and Backplate 4 Preparation: Select an acrylic resin, specifically polymethyl methacrylate (PMMA) in this embodiment, and form the upper cover 3 and backplate 4 through molding or 3D printing. This approach ensures better structural matching with the chip body 2.

Subsequently, clean and dry the PDMS-based chip body 2 sequentially with 95% alcohol and deionized water, followed by drying at 80° C. Perform the first oxygen plasma treatment on the surface of the chip body 2 to generate hydroxyl groups (—OH). Next, modify the PDMS surface by reacting 3-trimethoxysilylpropyl methacrylate (TMSPMA) with the hydroxyl groups (—OH) to achieve PDMS surface modification. Afterward, conduct the second oxygen plasma treatment on the TMSPMA-modified PDMS to obtain the surface-modified chip body 2. Subsequently, drop the hydrogel composition into the through-holes 24, and use a UV lamp (B-100AP lamp, 365 nm, 100 mW) to irradiate the hydrogel composition for 10 to 25 minutes, thereby solidifying it. This process fills the through-holes 24 with the dynamic hydrogel 5, resulting in a semi-finished product.

Surface Modification of Upper Cover 3 and Backplate 4: Clean the PMMA-based upper cover 3, which includes liquid inlet holes 32 and liquid outlet holes 33, and the PMMA-based backplate 4 sequentially with 95% alcohol and deionized water, then dry at 80° C. Perform the first oxygen plasma treatment on the bonding surfaces of the upper cover 3 and backplate 4 to generate hydroxyl groups (—OH). Subsequently, modify the surfaces by reacting 3-aminopropyltriethoxysilane (ATPES) with the hydroxyl groups (—OH) to obtain the surface-modified upper cover 3 and backplate 4.

Subsequently, bond the surface-modified upper cover 3 and backplate 4 to the opposite surfaces of the semi-finished product and apply pressure for at least 3 hours to create tight bonds between the upper cover 3, backplate 4, and the semi-finished product. This process completes the preparation of the lung fibrosis bionic chip in this embodiment.

Figure 3:
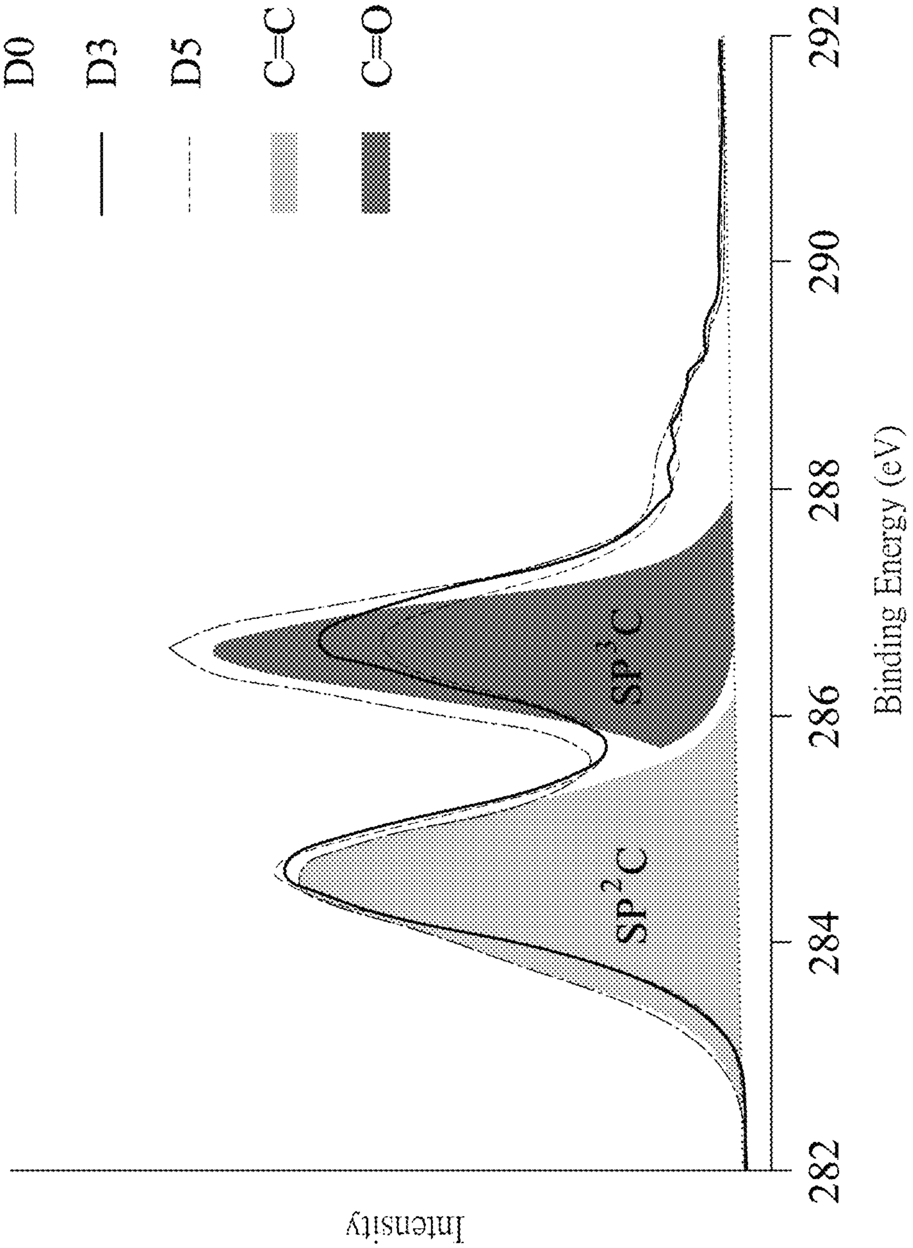
FIG. 3 is an XPS spectrum illustrating the absorption intensity of graphene oxide before annealing and after annealing for different durations at various energy gaps.
Figure 4:
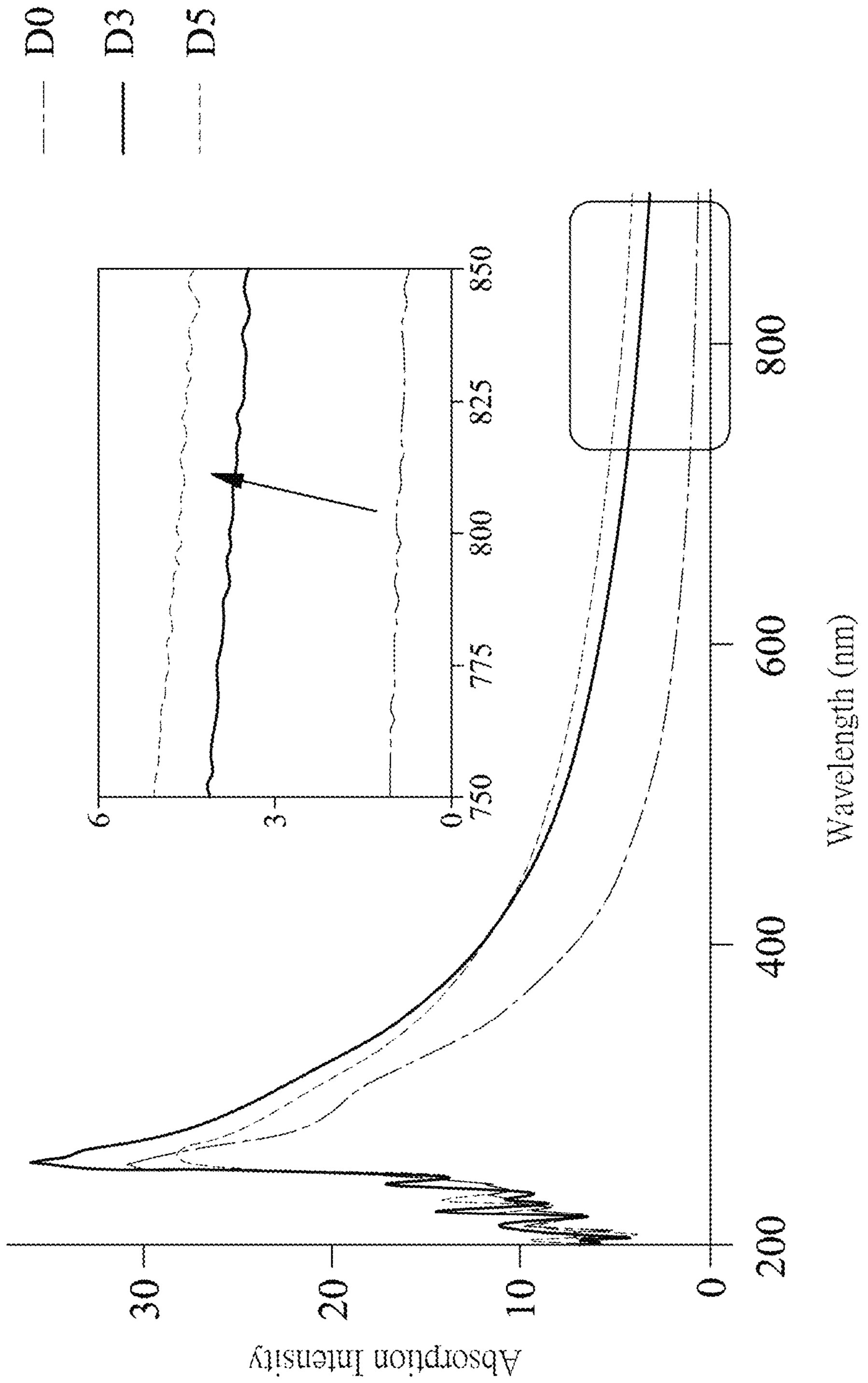
FIG. 4 is an absorption spectrum illustrating the absorption intensity of AGO before annealing and after annealing for different durations at various wavelengths.

Reference to FIGS. 3 and 4: FIG. 3 illustrates the X-ray photoelectron spectroscopy (XPS) results of graphene oxide (GO) after annealing for different days, while FIG. 4 depicts the full-wavelength absorption spectra of graphene oxide after annealing for varying days. Here, D0, D3, and D5 represent graphene oxide annealed for 0, 3, and 5 days, respectively.

Analysis of XPS and Absorption Results: As shown in FIG. 3 and FIG. 4, unannealed graphene oxide exhibits a higher $sp^3$-C absorption intensity compared to $sp^2$-C. With increasing annealing days, the $sp^3$ orbitals of graphene oxide gradually decrease, while the $sp^2$ orbitals correspondingly increase. However, the carbon-to-oxygen (C/O) ratio and the oxygen atom content remain unchanged. This indicates that annealing effectively enhances the $sp^2$ orbitals of graphene oxide without affecting the content of carbon and oxygen functional groups. Additionally, as the annealing duration increases, the light absorption capacity of the AGO in the visible light spectrum significantly improves. Specifically, graphene oxide annealed for 5 days demonstrates excellent light absorption in the visible light band, accompanied by a decreasing trend in UV light absorption.

In some embodiments, the content of AGO in the hydrogel composition ranges from 0.03 wt % to 0.15 wt %. As the AGO content increases, the regions containing AGO become denser, leading to a more densely distributed hydrogel composition. When the AGO content reaches a certain level, the edges of the AGO sheet structure begin to connect laterally, forming an interpenetrating network (IPN) structure with the crosslinked PNIPAM, resulting in a more uniform network structure. However, if the AGO content exceeds a certain amount, it affects gelation and makes gel formation difficult. Therefore, the optimal AGO content in the hydrogel composition ranges from 0.03 wt % to 0.075 wt %. Preferably, the AGO content in the hydrogel composition ranges from 0.0375 wt % to 0.075 wt %.

Figure 5:
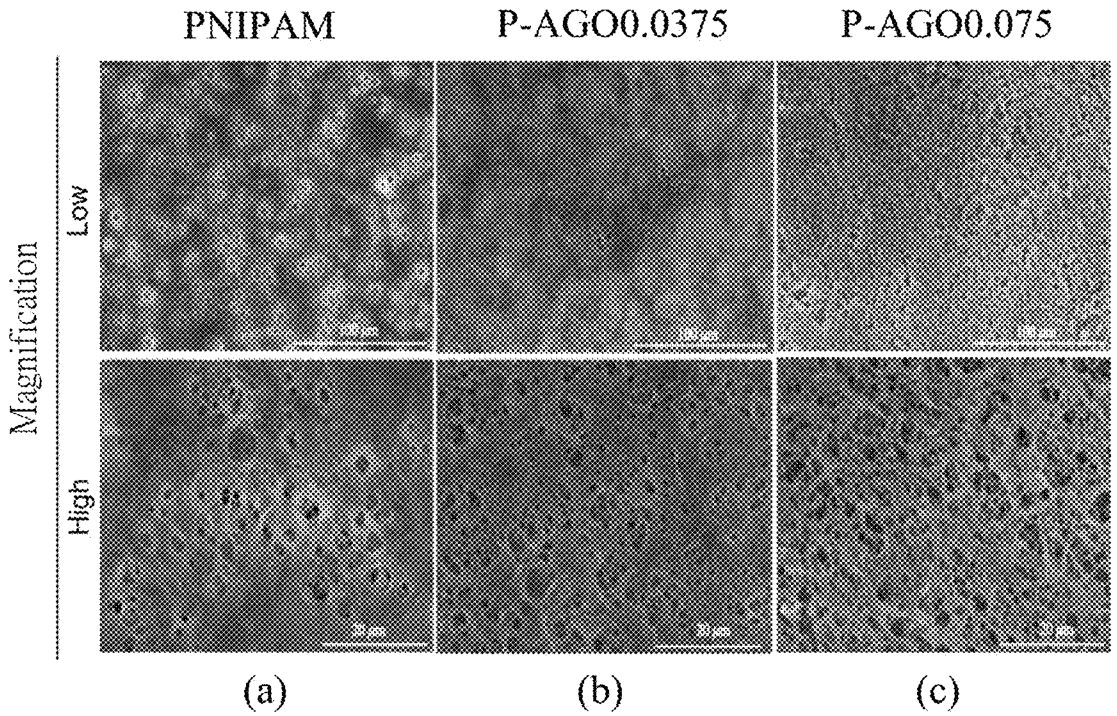
FIG. 5 is a scanning electron microscope (SEM) image illustrating the surface morphology of crosslinked PNIPAM, P-AGO0.0375, and P-AGO0.075.
Figure 6:
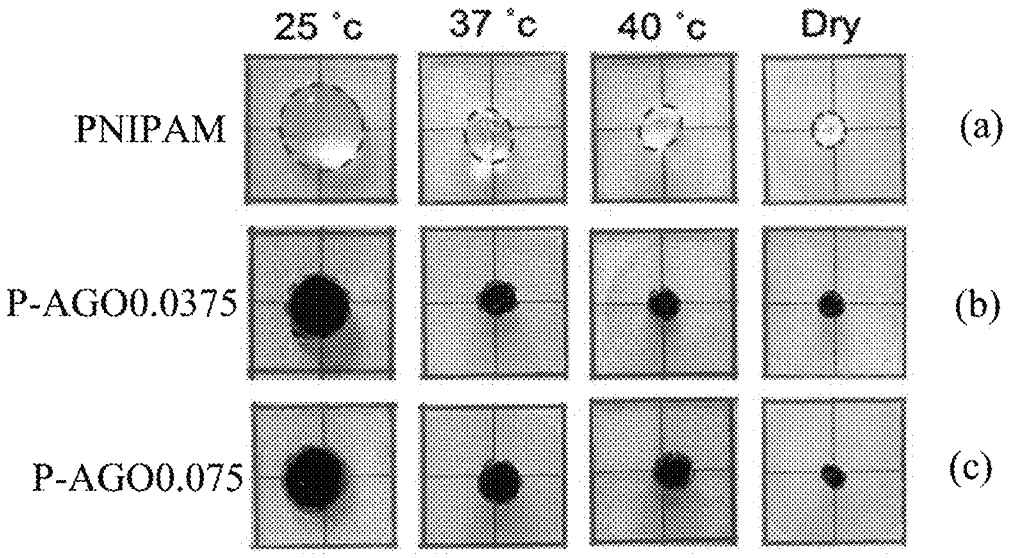
FIG. 6 is a deformation photograph illustrating the volumetric deformation results of crosslinked PNIPAM, P-AGO0.0375, and P-AGO0.075 at different temperatures.

Referring to FIG. 5 and FIG. 6, FIG. 5(*a*)-(*c*) show SEM surface morphology photos of crosslinked PNIPAM at the same UV light irradiation duration and dynamic hydrogels containing 0.0375 wt % and 0.075 wt % AGO (denoted as P-AGO0.0375 and P-AGO0.075, respectively). FIG. 6(*a*)-(*c*) show the volume of crosslinked PNIPAM at the same UV light irradiation duration and dynamic hydrogels P-AGO0.0375 and P-AGO0.075 under dry conditions, after reaching swelling equilibrium by soaking in deionized water at 25° C. for 24 hours, and the volume results when placed in a 37° C. and 40° C. environment after reaching swelling equilibrium at 25° C.

From the results in FIG. 5(*a*), it may be seen that the crosslinked PNIPAM itself forms a porous structure. With the increase in AGO content (FIG. 5(*b*)-(*c*)), a denser network structure and sheet-like structure may be observed on the surface. The formation of the hydrogel network facilitates material exchange and swelling absorption within the dynamic hydrogel. The results in FIG. 6(*a*)-(*c*) show that the dynamic hydrogel reaches swelling equilibrium at 25° C., and its volume changes (shrinks) as the temperature rises to 37° C. and 40° C. The dynamic hydrogel P-AGO0.075 with 0.075 wt % AGO has better water retention.

Figure 7:
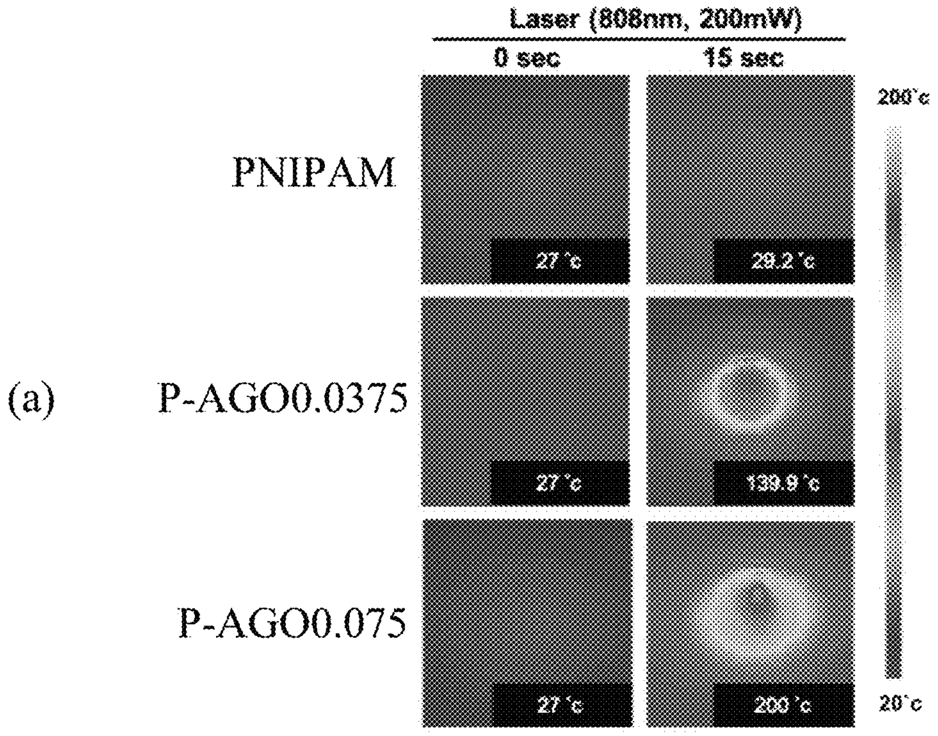
Figure 7:
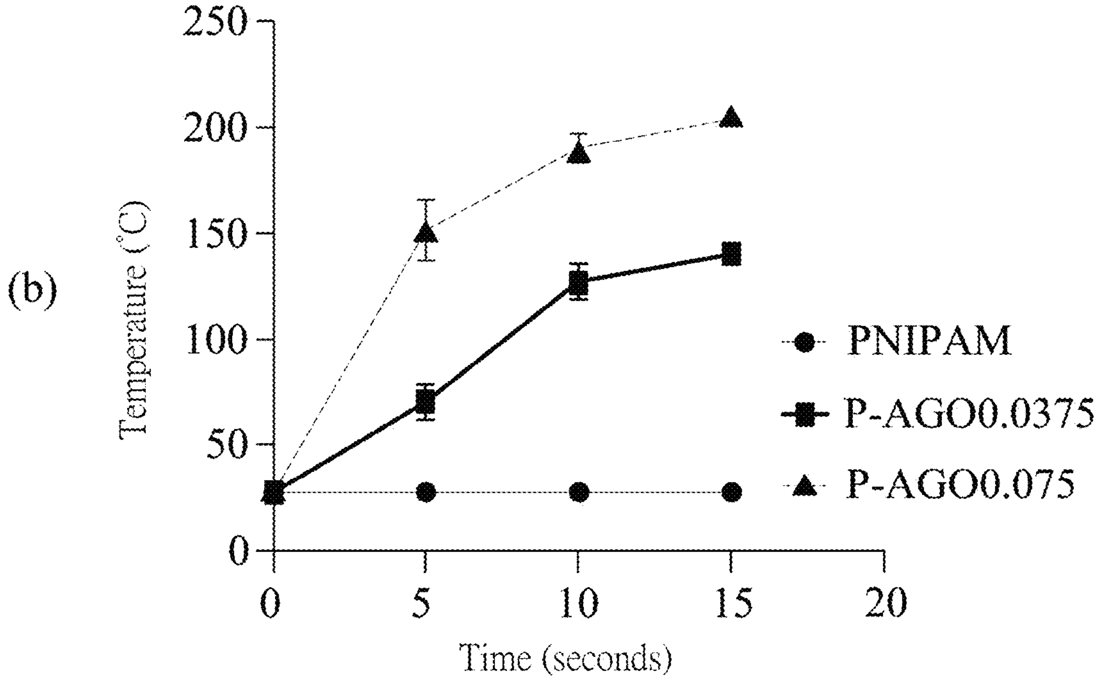

Referring to FIG. 7, it shows the temperature measurement results of crosslinked PNIPAM hydrogel and dynamic hydrogels containing 0.0375 wt % and 0.075 wt % AGO (denoted as P-AGO0.0375 and P-AGO0.075, respectively) after 15 seconds of irradiation with a near-infrared laser (808 nm, 200 mW). FIG. 7(*a*) shows the temperature measurement results using an infrared thermal imager after 15 seconds of laser irradiation, and FIG. 7(*b*) shows the time-temperature curve during the laser irradiation process. From FIG. 7, it may be seen that the temperature rise of PNIPAM hydrogel after 15 seconds of laser irradiation is not significant, but the photothermal conversion efficiency of the dynamic hydrogels with AGO is significantly improved. The temperature of the dynamic hydrogel P-AGO0.0375 may rise to about 140° C., and the temperature of the dynamic hydrogel P-AGO0.075 may even rise to 200° C. This shows that within the predetermined AGO content range, the higher the AGO content, the better the photothermal conversion efficiency of the dynamic hydrogel.

Figure 8:
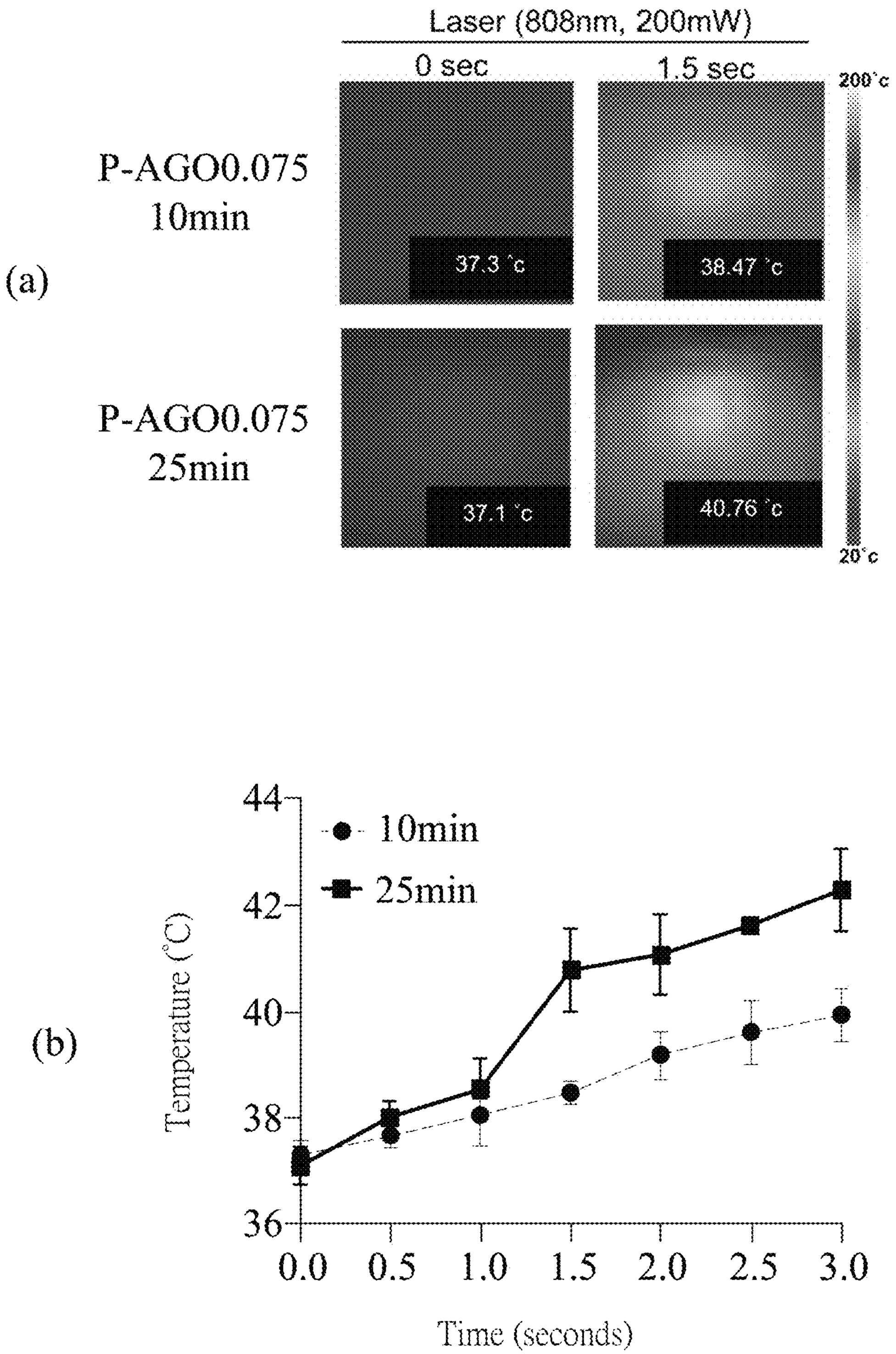

Next, the hydrogel composition containing 0.075 wt % AGO, which is crosslinked and cured by UV irradiation for 10 minutes and 25 minutes, is irradiated with a near-infrared laser (808 nm, 200 mW) for 3 seconds. The laser irradiation time simulated the thermal response corresponding to human breathing frequency, and the temperature change of the dynamic hydrogel during the irradiation process is measured. The longer the UV irradiation time, the higher the hardness of the resulting dynamic hydrogel. The temperature measurement results are shown in FIG. 8. From FIG. 8, it may be seen that after 1.5 seconds of laser irradiation, the temperature of the dynamic hydrogels may rise to the range of 38° C. to 40° C., with different gelation times (i.e., different UV irradiation times) affecting the temperature change by about 1° C. to 2° C. During the 3-second laser irradiation process, the harder dynamic hydrogel exhibits higher photothermal conversion efficiency. This shows that with the same AGO content, the photothermal conversion efficiency of the dynamic hydrogel may be further adjusted by controlling the crosslinking time (UV irradiation time).

Figure 9:
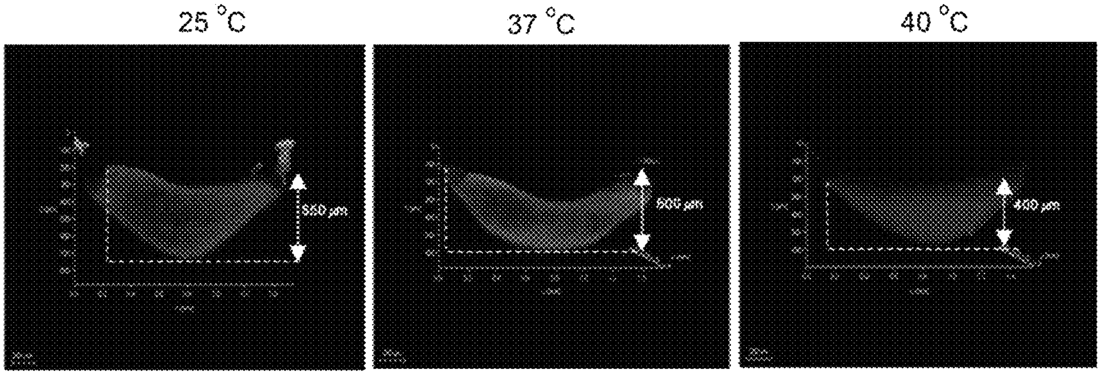
FIG. 9 is a confocal microscopy photograph illustrating the deformation states of the dynamic hydrogel in the lung fibrosis bionic chip at different temperatures.

To investigate the thermoresponsive deformation behavior of the dynamic hydrogel incorporated into the lung fibrosis bionic chip, the dynamic hydrogel is subjected to staining and subsequently observed under varying temperature conditions. The results of this observation are depicted in FIG. 9.

Specifically, the thermoresponsive deformation is assessed by preparing a staining solution including fluorescein isothiocyanate isomer I dissolved in Dulbecco's phosphate-buffered saline (DPBS) at a dilution ratio of 1:500. The staining solution is dispensed dropwise onto the dynamic hydrogel in the lung fibrosis bionic chip, wherein the dynamic hydrogel has been crosslinked via ultraviolet (UV) irradiation for 25 minutes. The dynamic hydrogel is allowed to stain for a duration of 2 hours. Subsequent to the staining process, the lung fibrosis bionic chip is immersed in water maintained at different temperatures (25° C., 37° C., and 45° C.). The deformation behavior of the dynamic hydrogel is observed utilizing confocal microscopy. The results, as presented in FIG. 9, demonstrate that the dynamic hydrogel exhibits a thickness of approximately 550 μm after swelling overnight at room temperature. Upon increasing the temperature to 37° C., the thickness is reduced to approximately 500 μm, and further increasing the temperature to 40° C. results in a thickness of approximately 4000 μm. These findings confirm that, when the temperature exceeds the LCST, the dynamic hydrogel achieves a deformation of approximately 27%.

Figure 10:
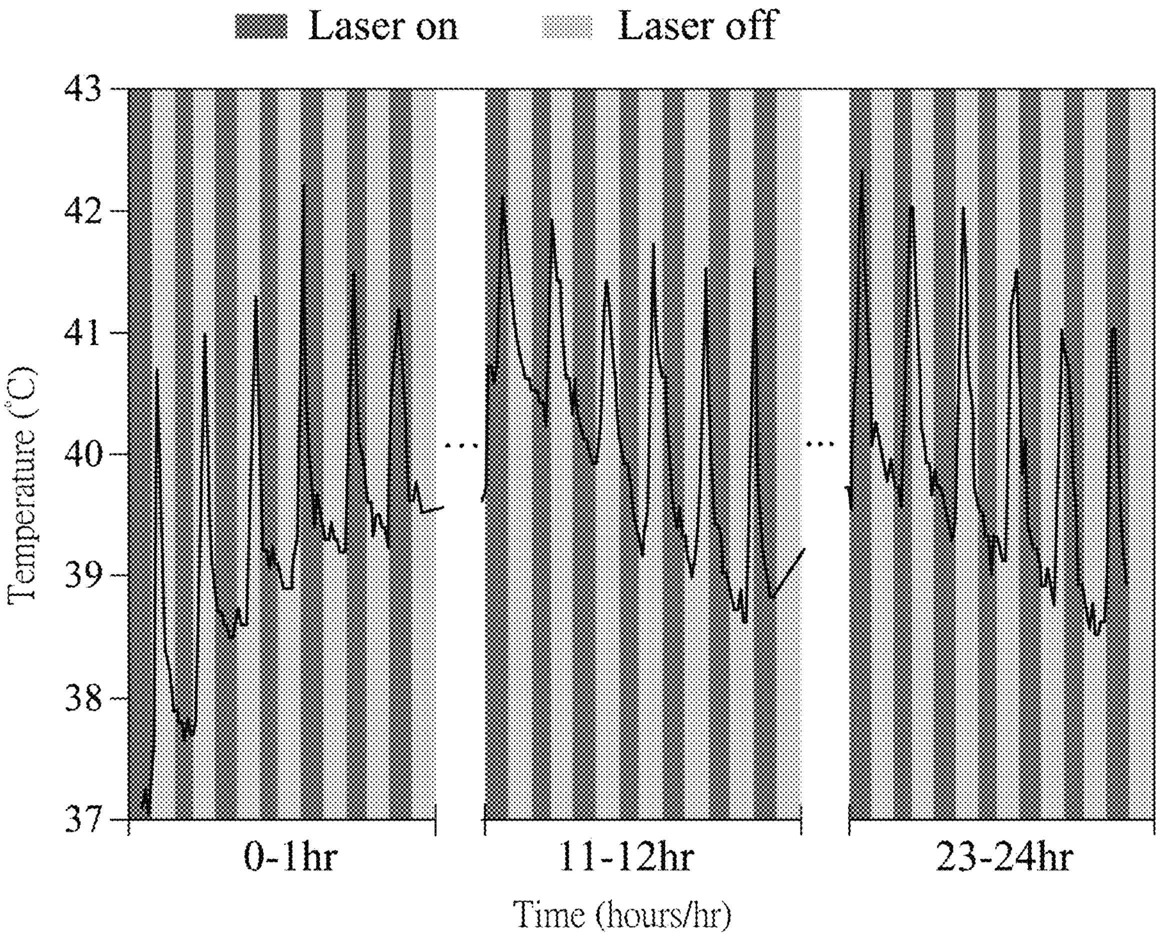
FIG. 10 is a time-temperature curve illustrating the thermal response results of the lung fibrosis bionic chip under prolonged laser irradiation.

A laser system is subsequently employed to irradiate the lung fibrosis bionic chip containing dynamic hydrogel 5. The dynamic hydrogel 5 is prepared by crosslinking the hydrogel composition via ultraviolet UV irradiation for a period of 25 minutes. The laser system utilized an 808 nm, 200 mW invisible light laser diode. The laser irradiation parameters are configured as follows: the laser open period (OP) is set to 1.5 seconds, the laser closed period (CL) is set to 3.5 seconds, and the loop operation (LOP) mode is configured for infinite cycles to facilitate continuous irradiation for a duration of 24 hours. Additionally, the laser irradiation mode is adjusted to operate on a 5-second cycle, corresponding to a simulated human respiratory rate of 12 Hz. The laser parameters are further modulated to simulate human respiratory rates ranging from 12 to 20 cycles per minute, enabling the observation of the thermoresponsive behavior of dynamic hydrogel 5 within the lung fibrosis bionic chip. The results, illustrated in FIG. 10, demonstrate that dynamic hydrogel 5 retains photothermal responsiveness even after 24 hours of continuous irradiation. These results further indicate that the dynamic hydrogel exhibits superior photothermal conversion efficiency, along with extended irradiation stability and cyclic tensile stress performance.

Establishment of IPF Chip Model

Next, to confirm the establishment of an IPF model using the lung fibrosis biomimetic chip of the invention, the dynamic hydrogel 5 of the chip has an AGO content of 0.075 wt %, and the UV irradiation crosslinking times are 10 minutes and 25 minutes, respectively.

Figure 11:
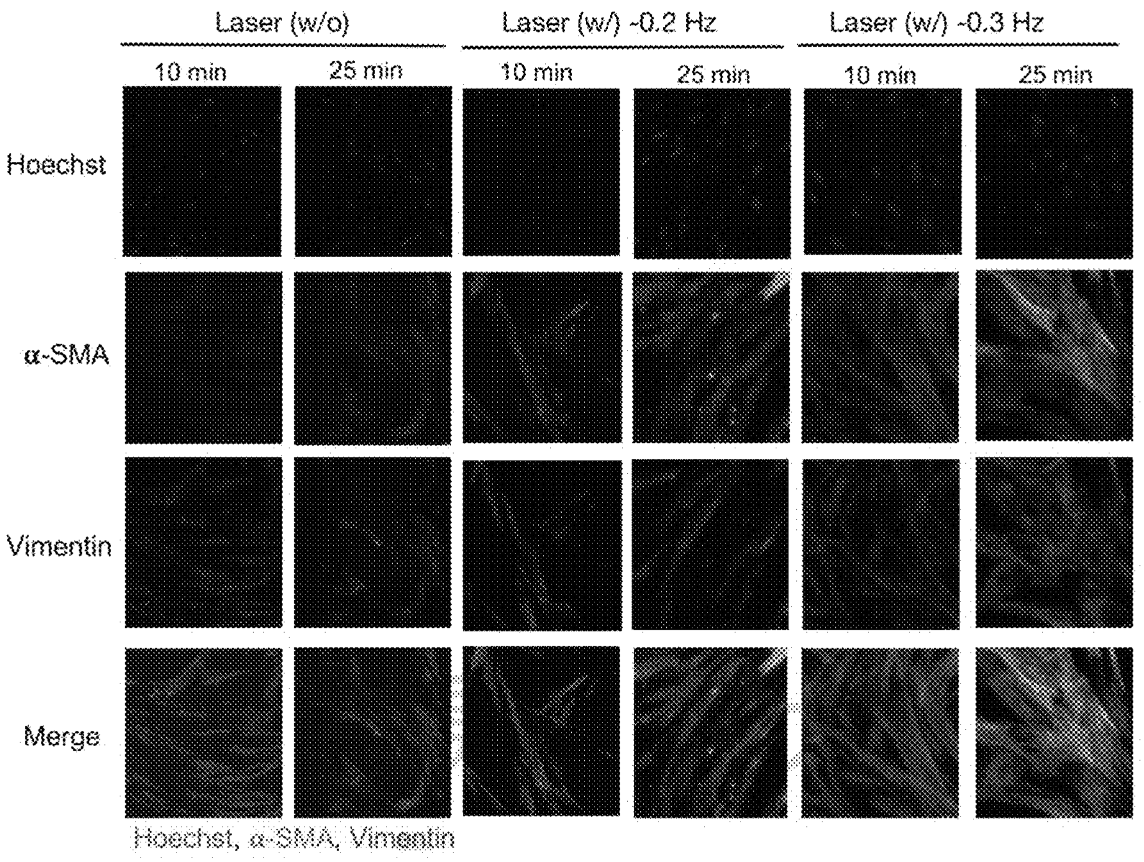
FIG. 11 is a fluorescence staining image illustrating the expression of fibrosis markers (α-SMA) in HFL-1 cells observed using immunofluorescence staining.

Using the dynamic hydrogel obtained from different crosslinking times as the cell culture substrate for fibrosis models (human fetal lung fibroblasts, HFL-1), the expression of α-SMA protein is used as an indicator of myofibroblast differentiation. After culturing the HFL-1 cells for one day, 10 ng/ml of TGF-β is added to stimulate the cells as a control group for α-SMA expression. After two days of culture, a laser device is used to irradiate the cells for 24 hours at frequencies of 0.2 Hz (On-1.5 s/Off-3.5 s) and 0.3 Hz (On-1.5 s/Off-1.5 s), respectively. The cells are then fixed and stained for observation. The results are shown in FIG. 11. In FIG. 11, "10 min" and "25 min" indicate the fluorescence images of the dynamic hydrogel 5 obtained by UV irradiation for 10 minutes and 25 minutes, respectively.

The immunofluorescence images in FIG. 11 show that HFL-1 cells cultured on the softer dynamic hydrogel (10 min) without laser response (Laser (w/o)) expressed vimentin but do not exhibit positive expression of α-SMA. Under dynamic frequency response laser irradiation (Laser (w/)-0.2 Hz and Laser (w/)-0.3 Hz), the fluorescence intensity of α-SMA stress fibers increases, and the cell morphology becomes more enlarged and flattened. Additionally, under high-frequency laser response combined with high-hardness dynamic hydrogel (25 min), the cell morphology appears the most flattened with the highest fluorescence intensity. This result indicates that the combination of a harder substrate and high-frequency laser response significantly enhances fibrosis expression compared to static culture.

Furthermore, since ECM remodeling in lung fibrosis patients leads to tissue stiffness, and stiff substrates apply mechanical stress to cells, the activity of YAP occurs through nuclear translocation, with YAP cellular localization depending on mechanical stress. Therefore, HFL-1 cells are cultured in dynamic hydrogels of different hardness (simulating substrates of varying stiffness) and dynamic response environments with laser frequencies to evaluate the effects of substrate hardness and dynamic response on the localization of YAP in lung fibroblasts. The results are shown in FIG. 12.

Figure 12:
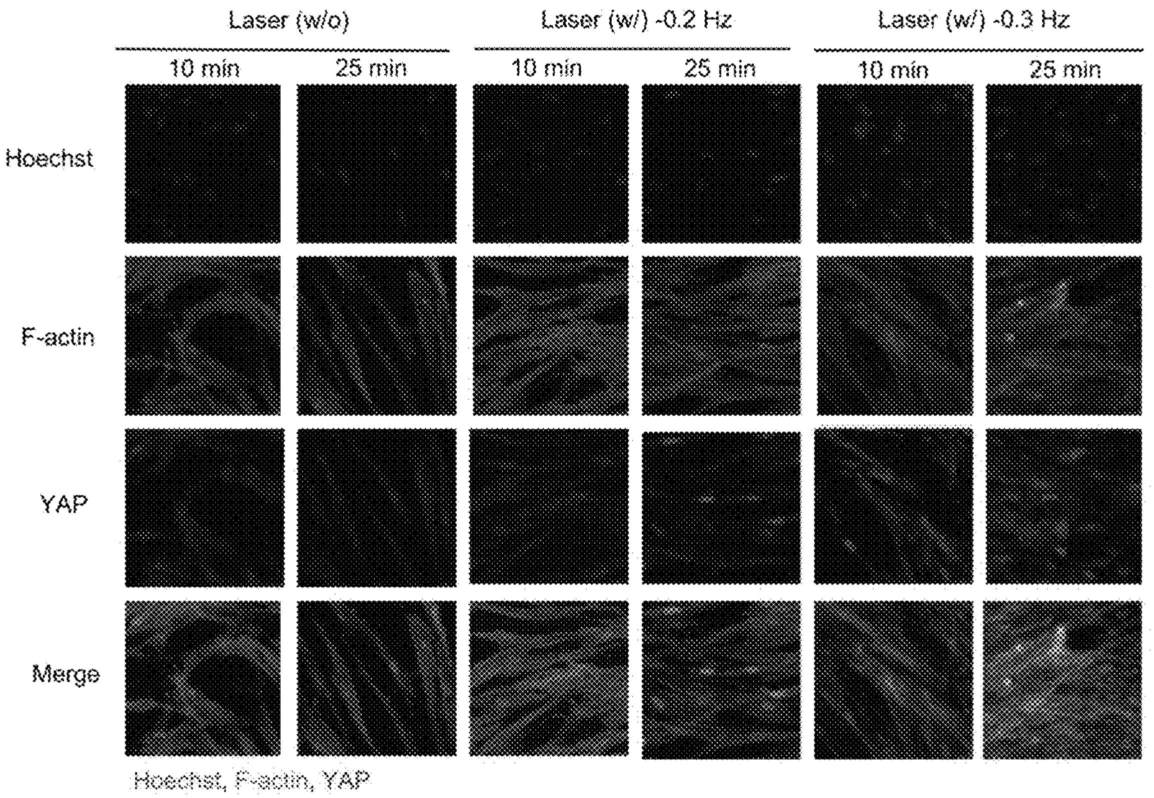
FIG. 12 is a fluorescence staining image illustrating the expression of mechanical response markers (YAP) in HFL-1 cells observed using immunofluorescence staining.

From FIG. 12, it may be seen that YAP cellular localization is sensitive to substrate stiffness. Without laser response (Laser (w/o)), cells cultured on the harder dynamic hydrogel (25 min) exhibit stretched morphology, and YAP is located in the nucleus. When subjected to laser frequency response, the cells display a more flattened and enlarged morphology compared to that of static culture, with increased fluorescence intensity and nuclear translocation of YAP, potentially accelerating fibrotic proliferation responses. This is consistent with current research indicating that stiff substrates promote increased fibrosis characteristics, with F-actin cytoskeleton transmitting mechanical signals to regulate YAP nuclear translocation. This also confirms that the lung fibrosis bionic chip of the invention may indeed be used to establish a lung fibrosis model.

Figure 13:
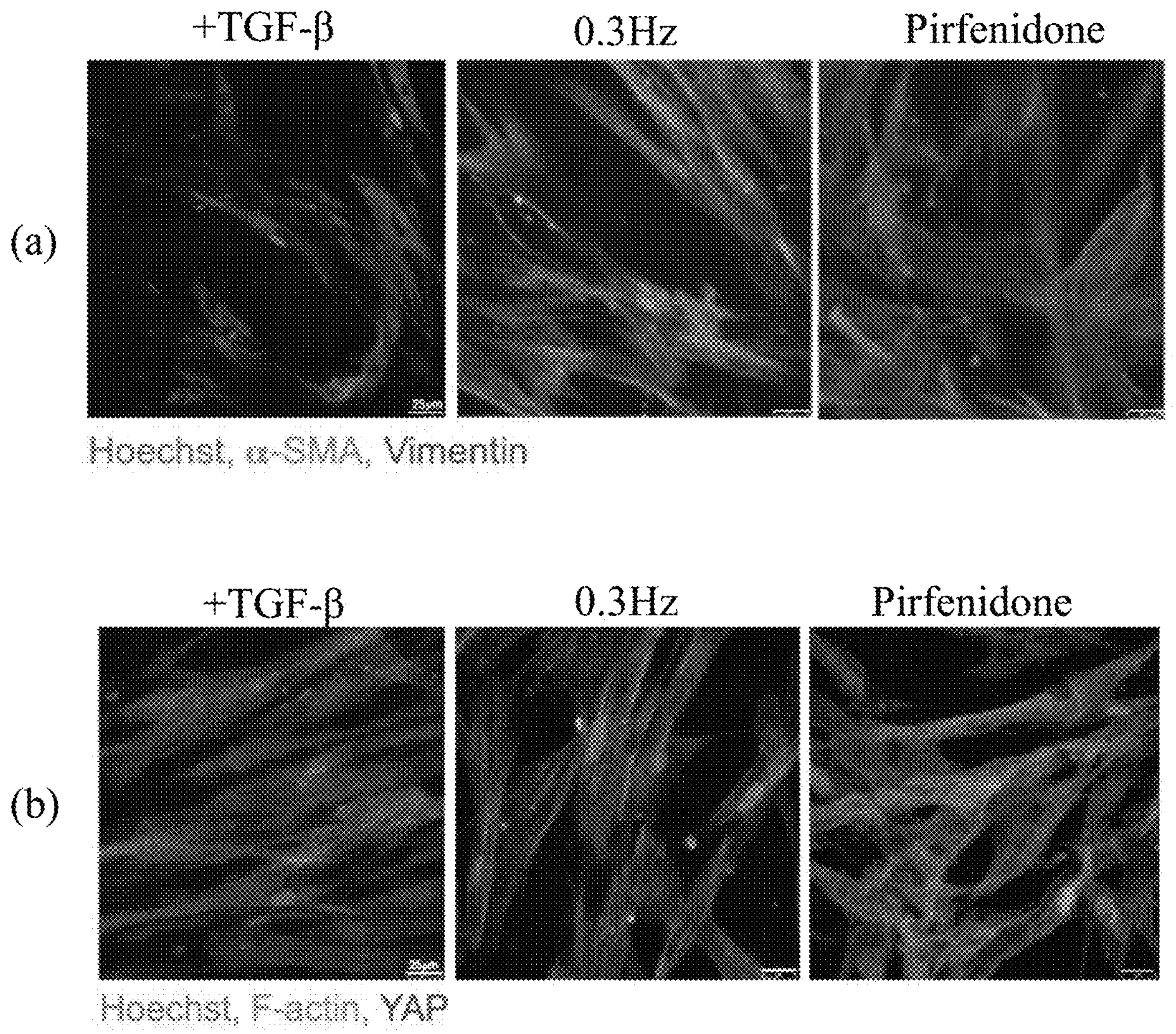
FIG. 13 is a fluorescence staining image illustrating the effects of the anti-fibrotic drug Pirfenidone in inhibiting fibrosis (a) and inhibiting mechanical responses (b) observed using immunofluorescence staining.

Next, the lung fibrosis bionic chip of the invention is used to establish a model for predicting the efficacy of antifibrotic drugs. The antifibrotic drug pirfenidone is used as an example. On the second day after culturing fibroblasts (HFL-1) on the dynamic hydrogel, TGF-β is used to induce fibrosis development in the HFL-1 cells. The dynamic response of the laser simulates the in vivo fibrotic lung state (including breathing frequency and lung tissue stiffness (dynamic hydrogel hardness)). Antifibrotic drugs are administered for two days until the end of the experiment. The results are shown in FIG. 13. In FIG. 13(*a*), it may be observed that after the addition of pirfenidone (5.3 mM), the expression of the fibrotic marker α-SMA in cells that originally exhibit a flat and fibrous morphology is inhibited. In FIG. 13(*b*), it is shown that pirfenidone has a less significant effect on inhibiting the mechanical response marker YAP, suggesting that the mechanism of pirfenidone in antifibrosis is unclear and not specific to the mechanical response pathway. This demonstrates that the lung fibrosis bionic chip of the invention may also be used to establish models for predicting the efficacy of antifibrotic drugs, making it suitable for drug screening, development, or other lung disease model establishments, thereby offering broader applications.

In summary, the present invention utilizes a hydrogel composition primarily based on the thermosensitive hydrogel PNIPAM, supplemented with GelMA and AGO. AGO enhances the photothermal conversion capability, thereby more effectively driving the thermal response of the dynamic hydrogel. Additionally, the addition of GelMA allows for further adjustment of the hardness of the resulting dynamic hydrogel through the control of UV irradiation time, enabling the simulation of varying stiffness levels associated with different lung fibrotic conditions. Consequently, the lung fibrosis bionic chip fabricated using the dynamic hydrogel as an ECM-mimicking material may elevate the deformation temperature of the hydrogel and mimic the stiffness range of lung diseases in vivo. This makes it more suitable for simulating the in vivo lung fibrosis environment in an ex vivo model, thereby achieving the objectives of the present invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A dynamic hydrogel deforming in response to heat, comprising:
- a hydrogel composition obtained by photo-crosslinking, comprising:
  - a photoinitiator;
  - poly (N-isopropyl acrylamide);
  - gelatin methacryloyl; and
  - annealed graphene oxide, wherein based on a weight percentage of 100 wt % of the hydrogel composition, the annealed graphene oxide is present in an amount ranging from 0.03 wt % to 0.15 wt %, and the X-ray photoelectron spectroscopy absorption intensity ratio of $sp^2$-C to $sp^3$-C ($sp^2$-C/$sp^3$-C) of the annealed graphene oxide is greater than 1.

2. The dynamic hydrogel of claim 1, wherein based on the weight percentage of 100 wt % of the hydrogel composition, the annealed graphene oxide is present in the amount ranging from 0.03 wt % to 0.1 wt %, and the gelatin methacryloyl is present in the amount ranging from 3 wt % to 8 wt %.

3. The dynamic hydrogel of claim 2, wherein based on the weight percentage of 100 wt % of the hydrogel composition, the annealed graphene oxide is present in the amount ranging from 0.0375 wt % to 0.1 wt %, and the gelatin methacryloyl is present in an amount ranging from 3 wt % to 5 wt %.

4. The dynamic hydrogel of claim 1, wherein after reaching swelling equilibrium, the dynamic hydrogel exhibits a volume deformation of at least 20% when heated from room temperature to a temperature above a lower critical solution temperature of poly (N-isopropyl acrylamide).

5. The dynamic hydrogel of claim 1, wherein the X-ray photoelectron spectroscopy absorption intensity ratio of $sp^2$-C to $sp^3$-C (sp2-C/sp3-C) of the annealed graphene oxide is between 1.09 and 1.3.

6. A lung fibrosis bionic chip, comprising:
- a chip body comprising:
  - a substrate having a first surface and a second surface opposing each other along a height direction;
  - at least one through-hole extending along the height direction and disposed in the substrate, wherein at least one end of the at least one through-hole is communicable externally, and the diameter of the at least one through-hole is between 1 mm and 5 mm; and
  - a dynamic hydrogel of claim 1 disposed in the at least one through-hole, and deformable upon heating.

7. The lung fibrosis bionic chip of claim 6, wherein the chip body further comprising:

a first groove and a second groove recessed downward from the first surface and the second surface of the substrate, respectively, the first groove and the second groove extend along a length direction of the chip body and are each communicable with opposite ends of the at least one through-hole; and the lung fibrosis bionic chip further comprising:

an upper cover and a backplate, wherein: the upper cover comprises:

a cover body; and multiple liquid inlet holes and multiple liquid outlet holes penetrating two opposite surfaces of the cover body; the cover body is connected to the first surface of the substrate and covers the first groove; the multiple liquid inlet holes correspond to liquid inlet ends of the first groove and the second groove; the multiple liquid outlet holes correspond to liquid outlet ends of the first groove and the second groove; and the backplate is connected to the second surface of the substrate and covers the second groove.

8. The lung fibrosis bionic chip of claim 7, wherein the substrate is selected from polydimethylsiloxane, and the cover body and the backplate are selected from acrylic resin.

9. The lung fibrosis bionic chip of claim 8, wherein the substrate is selected from polydimethylsiloxane surface-modified with 3-trimethoxysilylpropyl methacrylate; and the cover body and the backplate are selected from acrylic resin surface-modified with silanol.

* * * * *